United States Patent [19]

Nanaumi

[11] Patent Number: 4,718,416

[45] Date of Patent: Jan. 12, 1988

[54] LASER TREATMENT APPARATUS

[75] Inventor: Yasuaki Nanaumi, Kuroiso, Japan

[73] Assignee: Kabushiki Kaisha Toshiba, Kawasaki, Japan

[21] Appl. No.: 690,634

[22] Filed: Jan. 11, 1985

[30] Foreign Application Priority Data

Jan. 13, 1984 [JP] Japan .................................. 59-4381

[51] Int. Cl.$^4$ ............................................ A61B 17/36
[52] U.S. Cl. .................................................. 128/303.1
[58] Field of Search ..................... 128/303.1, 395–398, 128/6; 335/154; 250/227; 350/96.26

[56] References Cited

U.S. PATENT DOCUMENTS

| | | | |
|---|---|---|---|
| 3,467,098 | 9/1969 | Ayres | 128/395 |
| 4,146,856 | 3/1979 | Jaeschke | 335/154 |
| 4,327,738 | 5/1982 | Green et al. | 128/6 |
| 4,427,881 | 1/1984 | Ruell | 250/227 |
| 4,529,875 | 7/1985 | Brogardh et al. | 250/227 |

FOREIGN PATENT DOCUMENTS 1946693 8/1970 Fed. Rep. of Germany ... 350/96.20

OTHER PUBLICATIONS

"Multispot Laser Photocoagulation System Using a Fiber Bundle Scanner", Fujii et al., Applied Optics, Oct. 1982.

Rev. Sci. Instrum., vol. 51, No. 3, "Production of Flat Top Beam Profiles for High Energy Lasers"; Grojean et al.; 1980.

Primary Examiner—William E. Kamm
Assistant Examiner—Max F. Hindenburg
Attorney, Agent, or Firm—Finnegan, Henderson, Farabow, Garrett & Dunner

[57] ABSTRACT

Medical apparatus for performing treatment with a laser beam includes a laser oscillator generating a laser beam which is transmitted over an optical fiber to a hand piece including a plurality of rectangularly sectioned light guides, or kaleidoscopes, each having an incident end and an emission end. The kaleidoscopes are arranged in a side-by-side configuration in a hand piece. The emission end of the optical fiber is connected to an iron sleeve which is slidably mounted in the hand piece to permit movement of the iron sleeve in a direction parallel to lines connecting the ends of the kaleidoscopes. A plurality of electromagnets equal in number to the number of kaleidoscopes are mounted in the hand piece and aligned with the kaleidoscopes. Selective energization of the electromagnets is operable to optically couple the emission end of the optical fiber to incident ends of individual kaleidoscopes. The kaleidoscopes provide multiple internal reflections such that uniform energy distribution radiation patterns are formed at the emission ends of the kaleidoscopes. A plurality of such radiation patterns are obtained at the emission end of the hand piece in precise alignment. A protective transparent plate is detachably mounted to the emission ends of the kaleidoscopes and permit the hand piece to be placed directly in contact with the body part to be treated.

9 Claims, 14 Drawing Figures

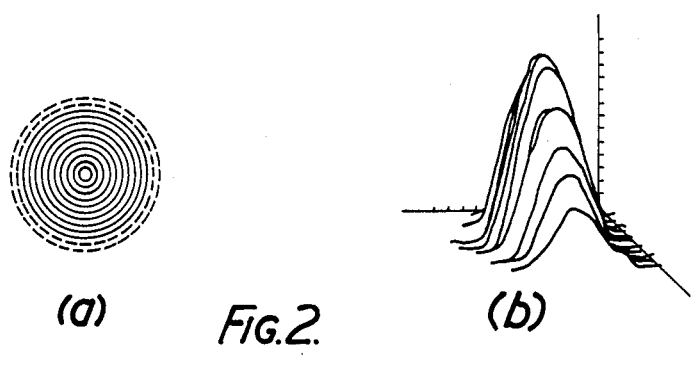
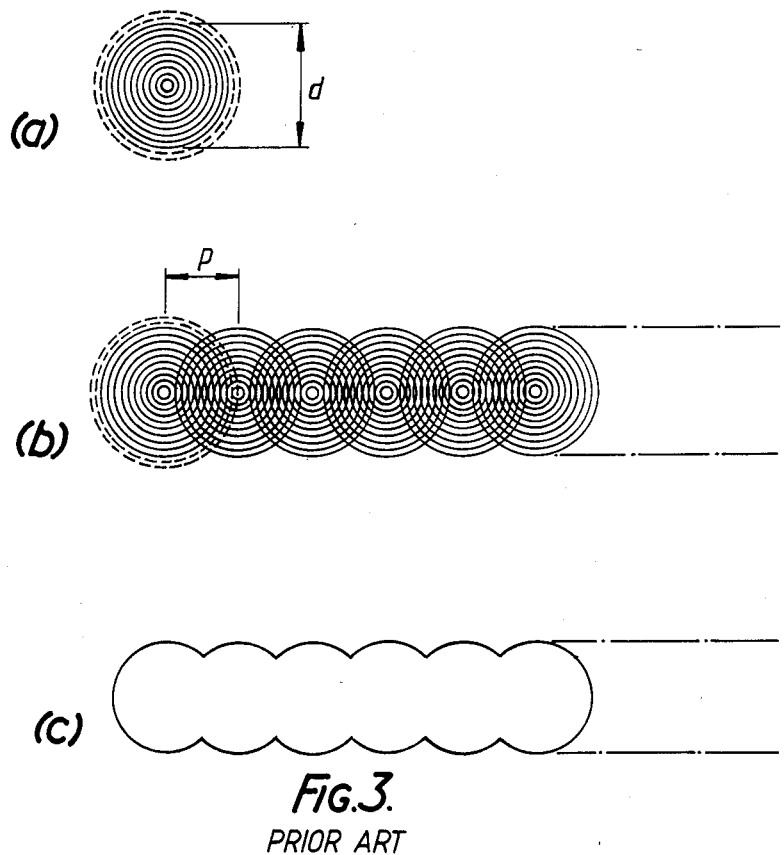
FIG. 2.
PRIOR ART
FIG. 3.
PRIOR ART

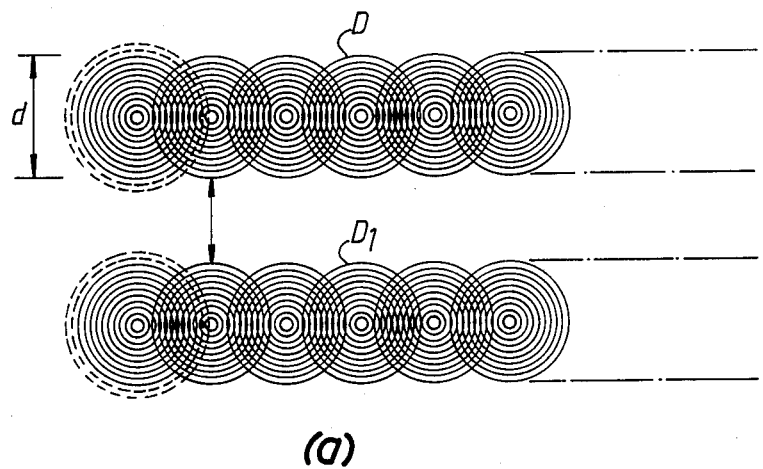
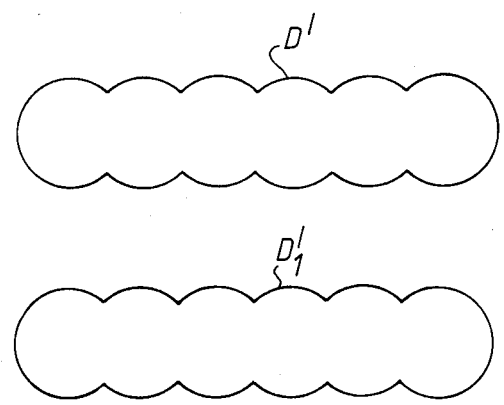
FIG.4.
PRIOR ART

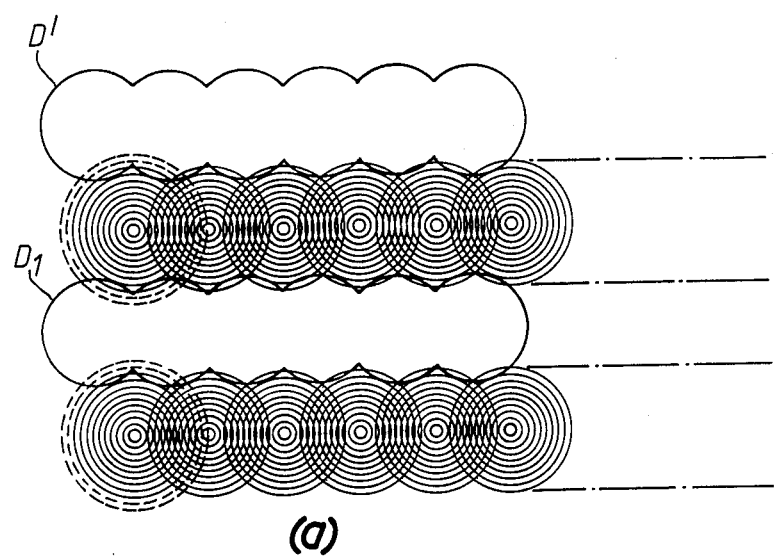
(a)
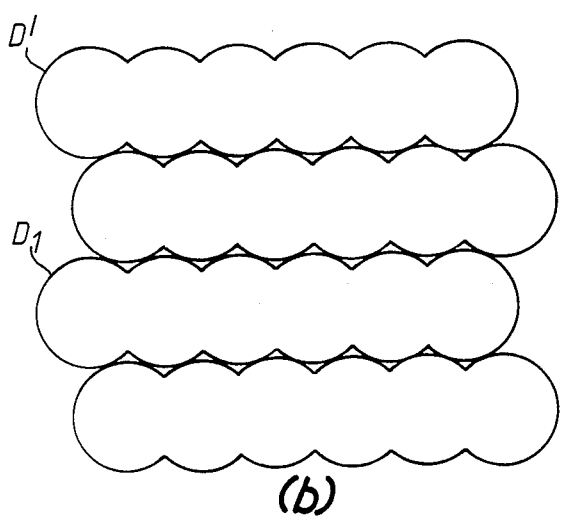
(b)
Fig.5.
PRIOR ART

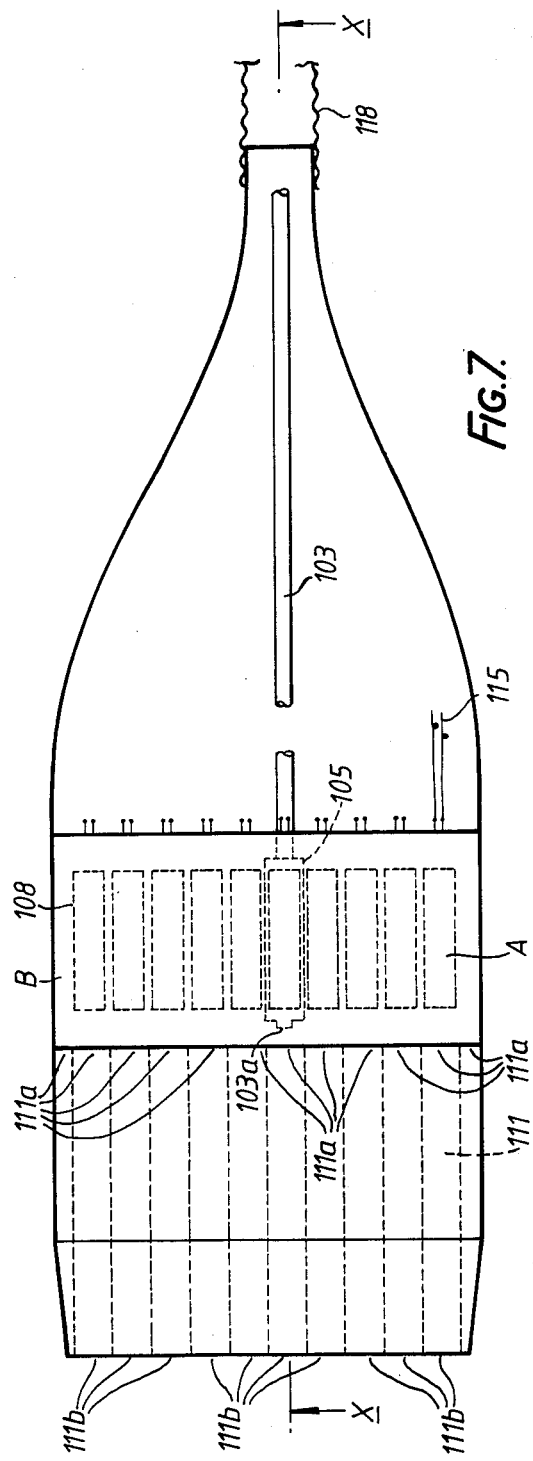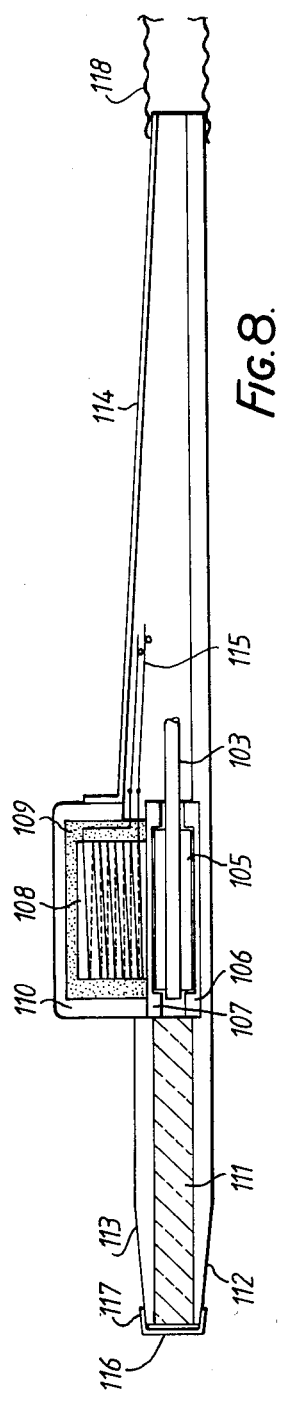

LASER TREATMENT APPARATUS

BACKGROUND OF THE INVENTION

This invention frelates to a laser treatment apparatus used, for example, in plastic surgery of dermatology, and, more particularly, to laser treatment apparatus which is adapted for the eradication or medical treatment of pigmented naevi consisting of abnormal blood vessels or pigmented cell agglomerations by radiating laser beams having a proper amount of energy onto said agglomerations.

Hitherto, various medical treatments of naevi have been attempted in the fields of surgery, dermatology and radiopathology. Such treatments have included surgical procedures such as excision, suture, skin grafting and surface skin exfoliation. In dermatology pharmacotherapy, dry ice and electrolysis treatment are used. Radiotherapy involves the application of radium, cobalt, strontium, etc. The above-listed processes may be considered the main types of medical treatment. However, these treatments have the drawback that despite the major invasion of the body a satisfactory therapeutic effect cannot be obtained. Moreover, surgical treatment is painful and sometimes requres long hospitalization. Consequently, there is a strong demand for improved treatment.

In recent years, histological research has been conducted to study the origin of the naevi, but progress is slow. Abnormal pigmented cells observed in, for example, the so-called vasuclar naevus are generally less transparent than normal cells, and absorb visible light rays more strongly than the normal transparent cells. Therefore, visible high energy light rays radiated on said abnormal cells are selectively absorbed, and changed into heat energy. As a result the abnormal cells are broker down due to intense burning. Conversely, the normal cells have higher transparency and absorb little of the above-mentioned high energy light rays, resulting in less heat damage. Consequently, the radiation of the aforementioned high energy light rays on the pigmented naevus causes only the abnormal cells to be selectively burnt off. In this case, the more transparent normal cells, perspiratory glands and tissue absorb little light, and are not irreversibly damaged. Therefore, the burnt normal cells and tissue are rapidly healed with only minute cicatrices remaining. Therefore, if it is possible to select such visible light wavelengths whose light energy is absorbed less by the normal cells of the naevus of the diseased spot and is absorbed to a greater extent by the pigmented cells, and if it is possible to set the energy density of said wavelengths at a prescribed level, then the pigmented cells canb e selectively destroyed. Laser beams represent light rays which satisfy the above-mentioned requirements.

At present, various laser medical apparatus have been proposed. FIG. 1 illustrates one such apparatus. Reference numeral 1 denotes an apparatus body. The body 1 comprises a power source 1A, a laser oscillator 1B and an operation panel 1C. Laser beams issue from laser oscillator 1B. They are conducted through an optical fiber 3 and ejected from the distal end of a hand piece 4. Argon laser rays, which have a typical wavelength of 5,140 A, and ruby laser rays, which have a typical wavelength of 6,943 A, provide a relatively large output of a visible light range effective for the treatment of pigmented naevi and are now being used in practical applications. Although ruby laser beams can provide high light energies and a broad radiation area, they have the drawback of being generated by pulse oscillation. This requires a longer overall radiation time, thereby lengthening the treatment period. Conversely, the argon laser beams have the drawback that they provide a lower light output (about several watts) than the ruby laser beams, but have the advantage that they can be better controlled and can be radiated on a relatively small area. Morover, they can be operated and handled at a higher speed and are more adapted for the treatment of a delicate structure.

The above-mentioned laser treatment apparatus is generally used by holding the hand piece 4. While the operator observes the diseased spot, the spot on which the laser beams are to be radiated is progressively shifted by an extent corresponding to the flux of the laser beams radiated from the end of the hand piece 4. The operator carries out treatment by radiating laser beams intermittently or continuously using a pedal switch, for example.

The energy intensity of the laser flux issued from the laser oscillatory progressively decreases from its center to its peripheral portion as seen from FIG. 2. This is called Gauss' distribution. FIG. 2a indicates Gauss' distribution by planar contour lines. FIG. 2b is a three-dimensional view of Gauss' distribution.

When laser beams having different energy intensities are radiated on a patient's diseased spot, radiation irregularities typically arise in accordance with the different energy intensities as shown in FIG. 3a. It is therefore necessary to apply an amount of radiation sufficient to heal the patient's diseased spot without causing ugly cicatrices or scars to be left at the central portion of said diseased spot in which highest laser beams energies tend to concentrate. The results of animal tests and clinical experience are being studied to determine the proper level of laser beam energy. At present, it is possible to determined the type of the patient reaction to laser beams and the extent of the cicatrices remaining according to the magnitude of the laser output and the volume of its flux (that is, the area of laser radiation). Further, it is possible to determine the efficiency of radiant heat and propagated heat by measuring the laser beam radiation time. It is also possible to define the moisture quantity in the case of thermal treatment and the cooling effect of blood by measuring the intervals at which laser beams are radiated.

FIG. 3b illustrates the case where a plurality of linearly arranged laser beam fluxes having a radiation diameter d are emitted under uniform conditions. It has been determined from clinical experience that the desired result can be attained if the pitch p between the respective laser beam fluxes corresponds to 30 to 40% overlap of the radiation diameter d. FIG. 3c shows the condition of a diseased spot which has been subjected to the radiation of laser beams and which has been healed after a certain lapse of time without any marks of cicatrices.

FIG. 4a shows the process of radiating laser beams on a patient's diseased spot. A plurality of laser fluxes are radiated so as to be linearly arranged in a partially superposed fashion "D". Thereafter, a similar group of laser fluxes are radiated near the above-mentioned laser fluxes at an interval $d_1$, which is smaller than the radiated diameter d of said laser fluxes. This second laser flux-radiated spot is referred to as "$D_1$". Namely, the radiation of laser fluxes is carried out in a zebra pattern.

This zebra pattern laser flux-radiating process is deemed the best method, the efficacy of which has been proved by experiments undertaken in regard to the effect of radiated heat and propagated heat and the cooling effect of the blood. FIG. 4b shows the patient's diseased spots which were subjected to the abovementioned zebra pattern laser flux-radiating process and which resulted in the healed conditions D', $D_1'$ after the lapse of a certain length of time.

FIG. 5a illustrates laser fluxes applied to the nonradiated intervening section of the zebra pattern laser flux-radiating process of FIG. 4b. FIG. 5b indicates the patient's diseased spots which were healed after a lapse of a certain length of time by the application of the zebra pattern laser flux-radiating process on the intervening spaces shown in FIG. 4a.

An actual medical operation with the above-mentioned laser apparatus is carried out in the following manner. The operator grips hand piece 4, and sets hand piece 4 perpendicular to the surface of the diseased spot. The operator holds hand piece 4 in such a manner that the output end face is at a predescribed distance from the diseased spot. While observing that portion of the diseased spot which is to be subjected to laser beams, the operator linearly moves the hand piece 4 to an extent corresponding to the total length of the plurality of laser fluxes linearly issued from hand piece 4 in succession and in a partially superposed fashion. The medical treatment is performed by continuously or intermittently radiating laser beams by actuating a pedal switch, for example. The reason why hand piece 4 is spaced away from the patient's diseased spot at a certain distance is to prevent the laser beam output from being reduced or the end face of the hand piece fiber from being broken due to the blood or flesh particles scattering from the diseased or applicated spot on said fiber end face during the laser treatment.

However, the surface of the diseased spot and the distal end of hand piece 4 are not generally brought into contact with each other. Therefore, it requires considerable skill to securely hold hand piece 4 perpendicularly to the diseased spot and at a prescribed distance. Further, tremendous difficulties are encountered in uniformly arranging with the naked eye the circles of the radiated laser fluxes (generally having a diameter of about 2 mm) or preserving a prescribed interval between the respective radiation circles of partially superposed laser fluxes arranged in the zebra pattern (i.e., an unradiated interval between the fluxes). If, therefore, the arrangement of the circular radaated laser fluxes is rendered irregular, and the respective radiated laser fluxes are superposed on each other to an excessive extent, the diseased spot may be noticeably destroyed, resulting in cicatrices remaining and harmfully affecting the laser treatment. If the respective groups of the radiated circular laser fluxes are spaced from each other too broadly, the intervening regions will remain untreated. If it is impossible to preserve the prescribed energy density of radiated laser fluxes (a function of the radiation time and the distance between the respective circles of radiated laser fluxes, assumingt that the laser output remains constant), then the respective laser fluxes tend to produce burnt marks. Laser fluxes having a greater energy density than is required for the temperature rise of the abnormal cells of the diseased spot are particularly likely to indiscrimately heat the surrounding non-diseased cells which require no laser treatment and thereby destroy normal cells.

As mentioned above, the conventional laser medical apparatus used in plastic surgery or dermatology has various drawbacks. When applied to practical medical treatment, the practicality of the conventional laser apparatus is reduced if the diseased spot is too broad. If the treatment continues for a long time, the operator will tire and the patient must maintain a certain posture for a long time without moving. Also, considerable difficulties are encountered in carrying out an effective laser treatment and the operator must use great skill.

It is therefore an object of this invention to provide laser apparatus featuring simpler positioning, lower skill requirements for operation, and effectively uniform irradiation.

Additional objects and advantages of the invention will be set forth in part in the description which follows, and in part will be obvious from the description, or learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purposes of the invention as embodied and broadly described herein, a laser treatment apparatus is provided which comprises means for generating a laser beam, a hand piece having an incident end and an emission end, and an optical fiber having an incident end connected to the generating means and an emission end connected to the hand piece. The optical fiber transmits the generated laser beam to the hand piece. The apparatus further comprises a plurality of means for uniformly distributing laser radiation, each of the distributing means having an incident end and an emission end corresponding to the hand piece incident and emission ends respectively. The distributing means are positioned side-by-side in the hand piece. The apparatus further comprises moveable means for optically coupling the optical fiber emission end to individual incident ends of the distributing means. The apparatus thus forms a plurality of uniform laser radiation patterns at the hand piece emission end. The apparatus may also include a transparent protective plate covering the hand piece emission end.

BRIEF DESCRIPTION OF THE DRAWINGS

The accompanying drawings, which are incorporated in and constitute a part of the specification, illustrate a preferred embodiment of the invention and, together with the general description of the invention given above, and the detailed description of a preferred embodiment given below, serve to explain the principles of the invention.

FIGS. 2(a) and (b) are a contour lines chart and a schematical perspective view, respectively, illustrating the intensity distribution of laser beams emitted from the hand piece of conventional laser treatment apparatus;

FIGS. 3(a), (b) and (c) are plan views illustrating irradiation examples and resulting tissue conditions obtained by irradiation of the affected part by use of the conventional laser treatment apparatus;

FIGS. 4(a) and (b) are plan views illustrating the state of zebra irradiation in use of the conventional laser treatment apparatus;

FIGS. 5(a) and (b) are a plan view illustrating radiation patterns of the conventional apparatus and a view illustrating the results of treatment by the apparatus, respectively;

FIG. 7 is a plan view illustrating a hand piece of the apparatus of FIG. 6;

FIG. 8 is a section view along the X—X line of FIG. 7; and

DESCRIPTION OF THE PREFERRED EMBODIMENTS

Reference will not be made in detail to the present preferred embodiment of the invention as illustrated in the accompanying drawings.

Figure 1:
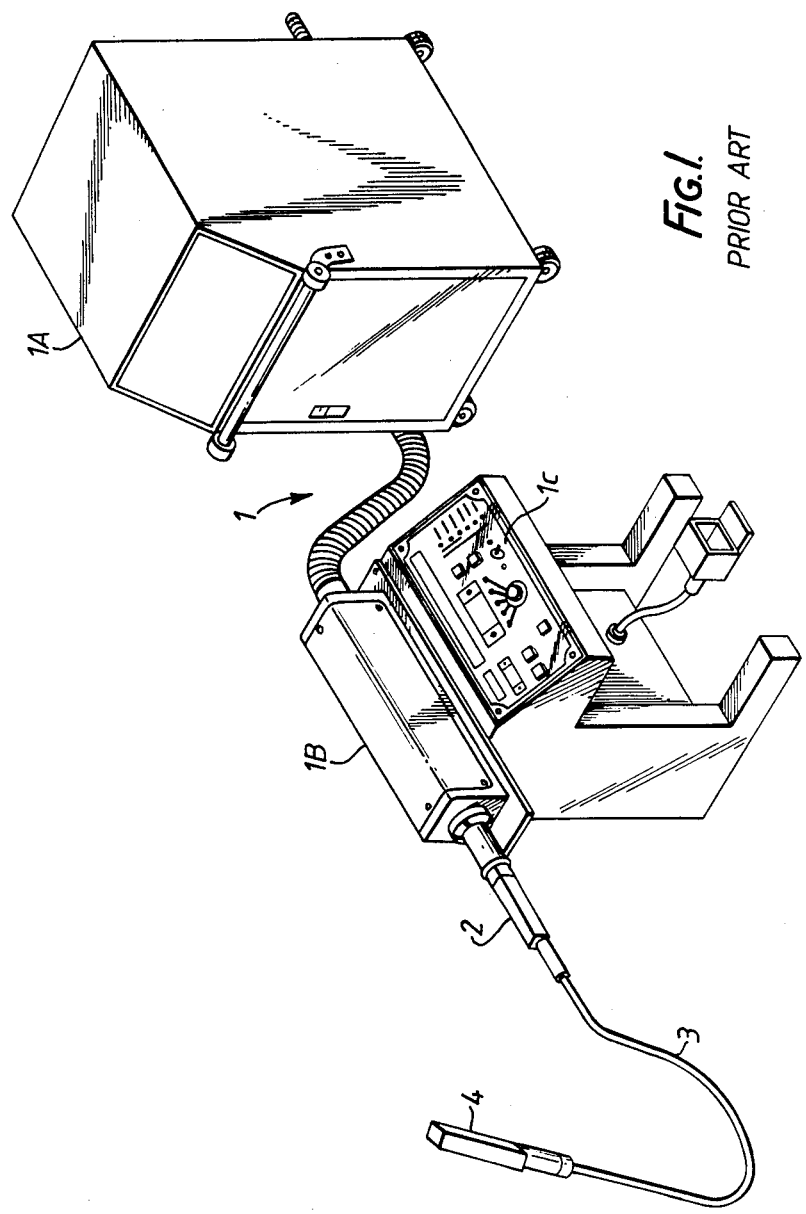
FIG. 1 is a perspective view illustrating conventional laser treatment apparatus.
Figure 6:
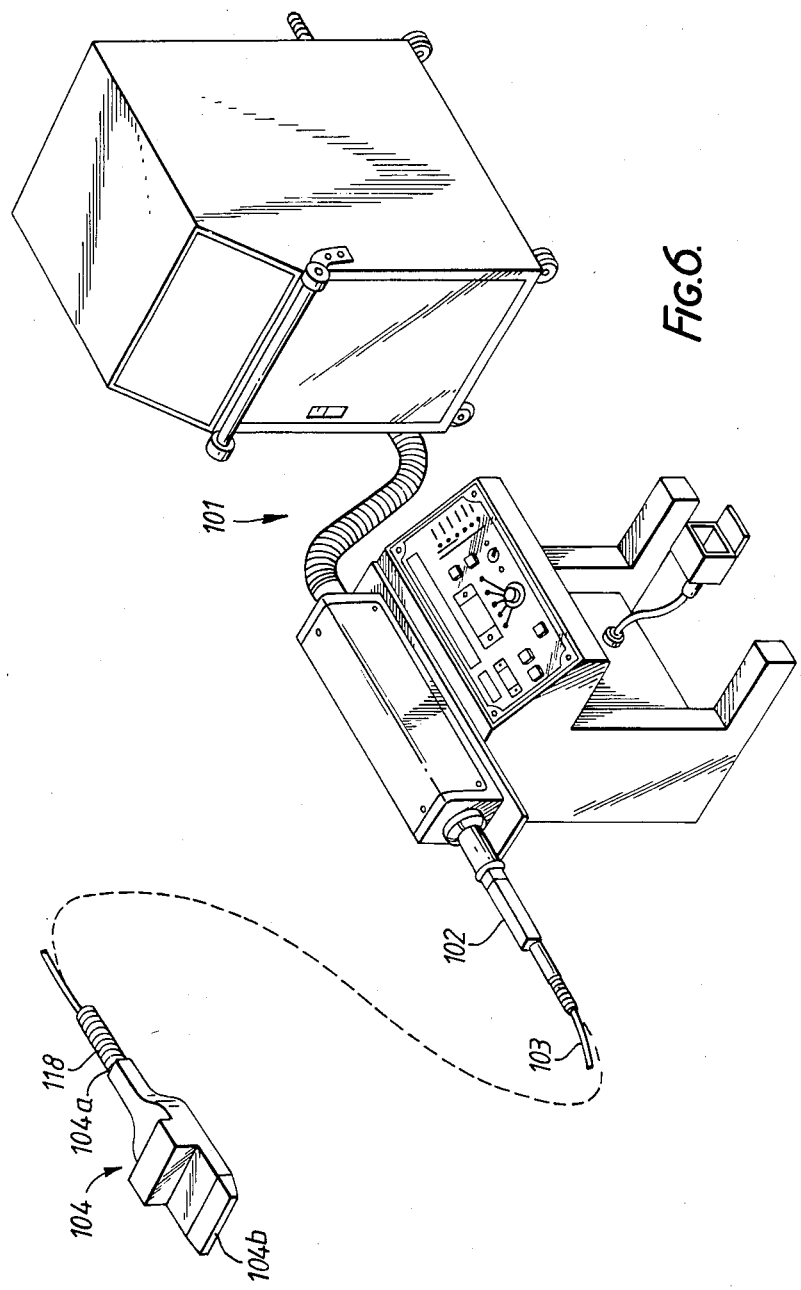
FIG. 6 is a perspective view illustrating the schematic construction of an embodiment of this invention.

FIG. 6 is a perspective view illustrating the schematic structure of the invention. The invention includes means for generating a laser beam. As embodied herein, the generating means includes a laser oscillator 101 and an incident adapter 102 which contains a condensing lens. Incident adapter 102 is connected to the incident end of an optical fiber 103 such that a generated laser beam from oscillator 101 is coupled to the incident end of optical fiber 103. The generated laser beam is transmitted over optical fiber 103 to a hand piece 104 having an incident end 104a and an emission end 104b. Hand piece 104 is optically coupled to the emission end 103a of optical fiber 103. Referring to FIGS. 7 and 8, the internal construction of the hand piece 104 is shown in detail. A plurality of rectangularly cross sectioned transparent pipe light guides, or optical conduits, known as kaleidoscopes 111, are mounted side by side adjoining in a row within hand piece 104 in a direction normal to the direction of a laser beam emerging from the emission end of optical fiber 103. Each of the kaleidoscopes 111 includes an incident end 111a and an emission end 111b respectively corresponding to the incident end and the emission end of hand piece 104 and has reflective internal surfaces. Kaleidoscopes 111 are mounted such that their incident end surfaces are positioned in a line and their emission ends surfaces are positioned in a line. A laser beam emerging from the emission end 103a of optical fiber 103 is optically coupled to the incident ends 111a of kaleidoscopes 111 to form a plurality of uniform laser radiation patterns at the emission end of hand piece 104. The invention thus includes a plurality of means for uniformly distributing laser radiation. As embodied herein, the distributing means includes kaleidoscopes 111.

The invention includes moveable means for optically coupling the optical fiber emission end to the individual incident ends of the distributing means. As embodied herein, the coupling means includes an iron sleeve 105 attached to the emission end 103a of the optical fiber 103 which is moveably mounted between a pair of guide cases 106 and 107. Space is provided between the guide cases 106 and 107 so that the sleeve 105 can move in reciprocation in a direction parallel to the lines defining the end surfaces of kaleidoscopes 111. The kaleidoscopes are also housed in a hand piece base member 112, being secured by a cover 113.

On the top of the upper case 107 are a plurality of electromagnets 108, equal in number to the number of kaleidoscopes 111, securely positioned by a non-magnetic holder 109. The holder 109 is protected by a cover 110. Each electromagnet 108 is aligned with a corresponding kaleidoscope 111.

The invention includes means for selectively energizing the electromagnets. As embodied herein, the energizing means includes lead wires 115 for supplying power to electromagnets 108 and a control unit (not shown) connected to wires 115 through a protective tube 118 which also contains the optical fiber 103. The control unit is provided with a plurality of electric changeover switches equal in number to the number of electromagnets, which switches sequentially and selectively energize electromagnets 108 to shift a magnetic field generating position upon the upper guide case 107. Due to the shift of magnetic field generating position, the sleeve 105 is moved in the same direction since it is attracted to the magnetic field generating position. As a result, the optical fiber 103 attached at its emission end 103a to the sleeve 105 is brought into the incident position of one of the kaleidoscopes 111. Therefore, since the laser beam is selectively sequentially brought incident to each of the kaleidoscopes, irradiation to a plurality of treatment lcoations is performed automatically by only a single position setting of the hand piece 104.

Furthermore, a protective plate 116 made of, for example, acrylic material and having good optical permeability is detachably mounted to the emission end of hand piece 104 by a suitable snap 117, to prevent dust in the atmosphere and contamination dispersed from the skin surface of a patient during treatment from being deposited on the laser emission end surface of each of the kaleidoscopes 111.

Operation of the inventive apparatus as constructed above will now be described. An operator first sets the laser output amount, radiant duration time, and energization time of electromagnets 108 and attaches the protective plate 116 in position at the emission end of hand piece 104 utilizing the snap 117. The operator then visually confirms the portion of the patient's body to be treated. While grasping the hand piece 104, the protective plate 116 is placed in close contact with the surface of the body portion to be treated. The emission end 103a of the optical fiber 103 is then positioned at either the electromagnet A or B in the most outer side of the hand piece 104, as shown in FIG. 7.

Generating a linear scan initiation signal by means of, for example, a foot switch, laser oscillation is produced in coordination with linear motion of the emission end of optical fiber 103 caused by selective energization of the electromagnets. As a result, the emission end 103a of the optical fiber 103 is shifted to the incident end of each kaleidoscope 111. After every such shift of the end surface of optical fiber 103, a laser beam is produced, thereby directing the laser beam to the incident end of the corresponding kaleidoscope to which the optical fiber incident end was shifted.

The laser beam is subjected to repeated reflection at the internal wall surfaces of the kaleidoscope, so that it is emitted from the emission end of each kaleidoscope with uniform energy distribution. This laser beam is automatically irradiated to the affected body part through the protective plate 116. Therefore, a plurality of laser radiation patterns with uniform energy intensity distribution are formed at the emission side end of the hand piece 104.

As described above, the apparatus is constructed such that using the optical fiber and a plurality of kaleidoscopes producing uniform energy intensity distribution, the emission end of the optical fiber is linearly moved along the direction of juxtaposition of the kaleidoscopes. Therefore, it is possible to establish uniform input irradiation to all of the kaleidoscopes. Also, it is possible to establish most precise irradiation over the whole emission end of the hand piece since laser beam irradiation over an extensive region is automatically performed with only a single setting of the hand piece upon the body part to be treated.

Furthermore, since the emission ends of the kaleidoscopes are protected from contamination by the protective plate 116, it is possible to place the hand piece directly in contact with the body part being treated, thus permitting precise location of radiation patterns in either a continuous pattern or a zebra pattern. Also, since a greater area may be irradiated with each positioning of the hand piece, a lower level of skill is required to operate the apparatus and the patient is not required to remain motionless in uncomfortable positions for long periods of time.

Figure 9:
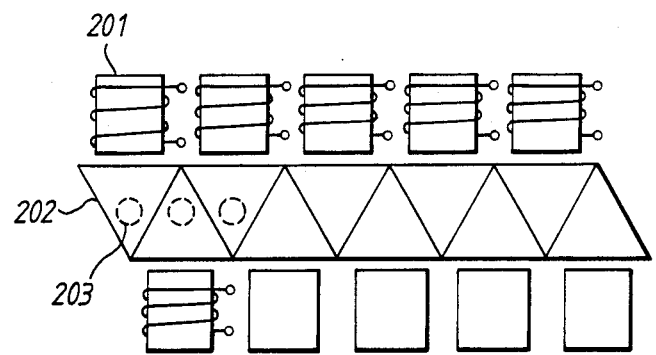
FIG. 9 is a schematical view showing kaleidoscopes and a portion of electromagnets from the hand piece emission end of another embodiment of the invention.

As should be apparent to those skilled in the art, modifications and variations can be made in the above disclosed embodiments without departing from the scope or spirit of the invention. For example, in the above-mentioned embodiment, the sectional configuration of the kaleidoscopes 111 have a rectangular cross section and the electromagnets 108 are disposed only on the upper guide case 107 in the hand piece 104. In an alternative embodiment shown in FIG. 9, a plurality of triangularly cross-sectioned kaleidoscopes 202 are alternately arranged in a straight line. Each cross section has an apex and a base. Kaleidoscopes 202 are arranged with the cross section base of each kaleidoscope aligned with the apex of an adjacent kaleidoscope. A plurality of electromagnets 201 are then disposed up and down alternately corresponding to the kaleidoscopes 202, respectively, to permit linear lateral movement of optical fiber 203.

Additional advantages and modifications will readily occur to those skilled in the art. The invention in its broader aspects is, therefore, not limited to the specific details, representative apparatus and illustrative example shown in described. Accordingly, departures may be made from such details without departing from the spirit of scope of applicant's general inventive concept.

I claim:

1. Laser treatment apparatus, comprising:
   means for generating a laser beam;
   a handpiece having an incident end and an emission end end;
   an optical fiber having an incident end connected to said generating means and an emission end connected to said handpiece, said optical fiber transmitting said generated laser beam to said handpiece incident end;
   a plurality of means for uniformly distributing laser radiation, each of said distributing means having an incident end and an emission end corresponding to said handpiece incident and emission ends, respectively, said distributing means being positioned side-by-side in said handpiece;
   a sleeve of magnetic material secured to the emission end of said optical fiber;
   a guide member mounted in said handpiece and movably securing said sleeve so as to permit movement of said sleeve in a direction parallel to said incident end surfaces to permit selective positioning of the emission end of said optical fiber in proximity to the incident ends of individual ones of said distribution means;
   a plurality of electromagnetc mounted in said handpiece, the energization of said electromagnets being operable to move said sleeve; and
   means for selectively energizing said electromagnets to selectively position the emission end of said optical fiber at the incident ends of said distributing means for form a plurality of specified uniform laser radiation patterns at said handpiece emission end.

2. Apparatus as recited in claim 1 wherein the number of said electromagnets is equal to the number of said distributing means.

3. Apparatus as recited in claim 2 wherein said energizing means energizes said electromagnets so as to sequentially position said optical fiber emission end at each of said distributing means incident ends.

4. Apparatus as recited in claim 1, wherein one of said distributing means comprises a pipe light guide providing multiple internal reflections; and one of said electromagnets is positioned in proximity to each pipe light guide.

5. An apparatus as recited in claim 1 where said emission end surfaces are disposed in a line and said apparatus further comprises:
   a detachably mounted substantially rigid transparent plate having a planar surface substantially parallel to said line of emission ends to protect said distributing means emission ends.

6. Laser treatment apparatus, comprising:
   means for generating a laser beam;
   a handpiece having an incident end and an emission end;
   an optical fiber having an incident end connected to said generating means and an emission end connected to said handpiece, said optical fiber transmitting said generated laser beam to said handpiece incident end and;
   a plurality of means for uniformly distributing laser radiation, each of said distributing means having an incident end and an emission end corresponding to said handpiece incident and emission ends, respectively, said distributing means being such that their incident end surfaces are positioned in a line and their emission end surfaces are positioned in a line;
   a sleeve of magnetic material secured to the emission end of said optical fiber;
   a guide member mounted in said handpiece and movably securing said sleeve so as to permit movement of said sleeve in a direction parallel to said line of incident end surface to permit selective positioning of the emission end of said optical fiber in proximity to the incident ends of inidividual ones of said distribution means;
   a plurality of electromagnets mounted in said handpiece, the energization of said electromagnets being operable to move said sleeve; and
   means for selectively energizing said electromagnets to selectively position the emission end of said optical fiber at the incident ends of said distributing means to form a plurality of specified uniform laser radiation patterns at said handpiece emission end.

7. An apparatus as recited in claim 6, wherein the number of said electromagnets is equal to the number of said distributing means.

8. An apparatus as recited in claim 7, wherein said energizing means energizes said electromagnets so as to sequentially position said optical fiber emission end at each of said distributing means incident ends.

9. An apparatus as recited in claim 6, further comprising:

a detachably mounted substantially rigid transparent plate having a planar surface substantially parallel to said line of emission ends to protect said distributing means emission ends.

* * * * *

UNITED STATES PATENT AND TRADEMARK OFFICE
CERTIFICATE OF CORRECTION

PATENT NO. : 4,718,416

DATED : January 12, 1988

INVENTOR(S) : Yasuaki NANAUMI

It is certified that error appears in the above-identified patent and that said Letters Patent is hereby corrected as shown below:

In Claim 1, Column 8, Line 3; change

"electromagnetc" to --electromagnets--.

In Claim 6, Column 8, Line 39; change

"and" to --end--.

Signed and Sealed this

Nineteenth Day of July, 1988

Attest:

DONALD J. QUIGG

Attesting Officer          Commissioner of Patents and Trademarks